United States Patent
Dawson

(10) Patent No.: US 9,693,752 B2
(45) Date of Patent: Jul. 4, 2017

(54) NON-RESISTIVE CONTACT ELECTROSONIC SENSOR SYSTEMS

(75) Inventor: Thomas Andrew Dawson, Aldershot (GB)

(73) Assignee: RESCON LTD, Crondall (GB)

( * ) Notice: Subject to any disclaimer, the term of this patent is extended or adjusted under 35 U.S.C. 154(b) by 581 days.

(21) Appl. No.: 13/527,862

(22) Filed: Jun. 20, 2012

(65) Prior Publication Data

US 2012/0330108 A1 Dec. 27, 2012

Related U.S. Application Data

(60) Provisional application No. 61/572,303, filed on Jun. 21, 2011.

(51) Int. Cl.
| | | |
|---|---|---|
| *A61B 7/02* | (2006.01) | |
| *A61B 7/00* | (2006.01) | |
| *A61B 5/04* | (2006.01) | |
| *A61B 5/00* | (2006.01) | |

(52) U.S. Cl.
CPC .......... *A61B 7/026* (2013.01); *A61B 5/04005* (2013.01); *A61B 7/00* (2013.01); *A61B 5/6844* (2013.01); *A61B 5/6886* (2013.01); *A61B 2562/066* (2013.01)

(58) Field of Classification Search
CPC .......... A61B 2562/066; A61B 5/04005; A61B 5/6844; A61B 5/6886; A61B 7/00; A61B 7/026
USPC ....... 600/54, 548, 6, 530, 407, 160, 37, 438, 600/411, 202; 607/3, 89, 116; 601/2–4; 606/41
See application file for complete search history.

(56) References Cited

U.S. PATENT DOCUMENTS 3,997,793 A * 12/1976 Rogers .................. G01T 1/2907
378/205
5,394,875 A * 3/1995 Lewis .................. A61B 8/0833
128/916
5,687,737 A 11/1997 Branham et al.
(Continued)

FOREIGN PATENT DOCUMENTS

| WO | 9207509 A1 | 5/1992 |
|---|---|---|
| WO | 2005072607 A1 | 8/2005 |
| WO | 2013124735 A1 | 8/2013 |

OTHER PUBLICATIONS

Harland et al., "Applications of Electric Potential (Displacement Current) Sensors in Human Body Electrophysiology", Proc. 3rd World Congress on Industrial Process Tomography, Banff, Canada, 2003, pp. 485-490.*

(Continued)

*Primary Examiner* — Katherine Fernandez
(74) *Attorney, Agent, or Firm* — Tillman Wright, PLLC; Chad D. Tillman; Jeremy C. Doerre

(57) ABSTRACT

A method of correlating sonic activity with electric activity in an entity of interest includes interrogating, via a sonic sensor device, the physical structure, shape and/or form of an object in the entity of interest, interrogating, via an electric field sensor, the electric and/or magnetic potential associated with the object or the physical displacement of the geo-electric field by the object while avoiding resistive contact with other portions of the entity of interest, and linking results from the sonic sensor device to results from the electric field sensor.

20 Claims, 15 Drawing Sheets

(56) References Cited

U.S. PATENT DOCUMENTS

| | | | |
|---|---|---|---|
| 6,678,552 B2* | 1/2004 | Pearlman | A61B 5/0536 600/547 |
| 6,952,606 B2* | 10/2005 | Anderson et al. | 600/547 |
| 2003/0045799 A1* | 3/2003 | Bazin | A61B 5/448 600/476 |
| 2006/0085049 A1* | 4/2006 | Cory | A61B 5/0536 607/48 |
| 2007/0270703 A1 | 11/2007 | He et al. | |
| 2008/0249375 A1* | 10/2008 | Obel | A61N 1/372 600/301 |
| 2009/0254134 A1* | 10/2009 | Nikolov et al. | 607/3 |
| 2010/0160737 A1* | 6/2010 | Shachar et al. | 600/202 |
| 2013/0060156 A1* | 3/2013 | Gregg | A61B 5/04011 600/523 |
| 2013/0253843 A1 | 9/2013 | Dawson et al. | |

OTHER PUBLICATIONS

Salgaonkar et al., "Passive cavitation imaging with ultrasound arrays", J. Acoust. Soc. Am., vol. 126, Issue 6, Dec. 2009, pp. 3071-3083.*

Roelandt, "A personal ultrasound imager (ultrasound stethoscope), a revolution in the physical cardiac diagnosis!", European Heart Journal, vol. 23, 2002, pp. 523-527.*

Shue, Karen. "The Basics of Brain Waves" Archived by the Internet Archive on Jun. 7, 2013: <http://www.brainandhealth.com/Brain-Waves.html>. pp. 1-3.

Pradhan, Cauchy; Jena, Susant K.; Narar, Sreenivasan R.; Pradhan, R. "Higher-Order Spectrum in Understanding Nolinearity in EEG Rhythms" Archived by the Internet Archive on Jun. 7, 2013: <http://www.hindawi.comm/journals/cmmm/2012/206857/>. pp. 1-6.

Quiroga, Rodrigo Quian. "Quantitative analysis of EEG signals: Time-frequency methods and Chaos theory" Archived by the Internet Archive on Jun. 7, 2013: <http://www.vis.caltech.edu/~rodri/papers/thesis.pdf> pp. 1-146.

"IC design using Electric Potential sensor technology to be announced at Sensors Expo" http://www.ecnmag.com/news/2011/06/ic-design-using-electric-potential-sensor-technology-be-announced-sensors-expo, accessed Dec. 1, 2014, 2 pages.

"New Biosensor Chip Picks Up Heart Signal Remotely" Jones, Willie D., Nov. 1, 2011, http://spectrum.ieee.org/biomedical/bionics/new-biosensor-chip-picks-up-heart-signals-remotely, accessed Nov. 1, 2014, 1 page.

"International Preliminary Report" and "Written Opinion of the International Search Authority" (European Patent Office) in Rescon Ltd, International Patent Application Serial No. PCT/IB2013/000587, dated Sep. 4, 2014, 7 pages.

* cited by examiner

NON-RESISTIVE CONTACT ELECTROSONIC SENSOR SYSTEMS

CROSS-REFERENCE TO RELATED APPLICATION

The present application is a U.S. nonprovisional patent application of, and claims priority under 35 U.S.C. §119(e) to, U.S. provisional patent application Ser. No. 61/572,303, filed Jun. 21, 2011, which provisional patent application is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

Field of the Present Invention

The present invention relates generally to non-resistive contact electrosonic sensor systems, and, in particular, to non-resistive contact sensors and sensor systems including devices and installations for detecting sonar signatures and electric or magnetic potentials.

Background

Auscultation is a widely used diagnostic procedure that provides a high degree of diagnostic power, is readily available, is non-invasive and can be performed at a relatively low cost. Typically, auscultation is performed using a stethoscope that acquires and conveys sounds or vibrations from the surface of a patient's body to an examiner's ear. More recently electronic stethoscopes have started replacing their mechanical counterparts. Electronic stethoscopes are typically based on a transducer that is capable of converting sounds or vibrations into electrical signals that are then amplified. Additionally, the detection capabilities of electronic stethoscopes are not limited to the constraints of human hearing. The effectiveness of human hearing varies substantially as a function of frequency and amplitude of the sounds to be detected. As a result, human hearing provides limited diagnostic capabilities because certain low frequency and/or low amplitude sounds that are useful for diagnostic purposes may be undetectable by humans. Electronic stethoscopes in combination with recent advances in signal processing and other technologies have resulted in the development of systems that can automatically acquire and analyze biological sounds or vibrations. Applications for electronic stethoscopes vary widely and include, for example, phonocardiology, phonopneumography and phonogastroenterology. In addition ultrasound stethoscopes have also been developed in response to the need to interrogate cardiac and breath sounds in environments where there may be high levels of ambient noise which can reach up to 110 dB during medical evacuation in a UH-60, BlackHawk helicopter.

Unfortunately, these solutions do not provide information on the electrical integrity of the heart or surrounding tissues. Traditionally resistive contact sensors are used which require electrical contact with the surface of individuals for effective transduction of the biological surface potential into an electronic format.

Combinations of acoustic stethoscopes and contact electrodes have been developed within the same device to effect the combined interrogation of structural and electrical function of the myocardium. This strategy however does not allow the flexibility that is needed in real life situations and the need for direct contact with the skin with the electrodes can be limiting especially when skin integrity is compromised secondary to injury or disease. Furthermore, resistive contact electrodes draw current away from the source, thus corrupting the signal, making reconstruction more technically challenging.

The problems with contemporary technologies may be summarized as follows. Sonar or other sonic sensing does not provide electrical information, and the results are corrupted by external acoustic and other sonic noise. Electric sensing, such as that involved in electrocardiograms, electromyograms, electroencephalograms, and the like, requires resistive contact, measuring the surface electric potential of the organism. In emergency situations, or when the surface is compromised, this approach can make it difficult to efficiently get a clear signal. Also, due to the resistive contact, the signal is drawn away from the source, making signal reconstruction difficult. Finally, existing electric and sonar and other sonic combinations require resistive contact, thus measuring only the surface potential and drawing the signal away from the source. In view of these problems, a need exists for an improved combination of electric and acoustic sensing.

SUMMARY OF THE PRESENT INVENTION

The present invention relates to methods by which sensors are combined in a novel fashion and the sensor data is utilized for detecting properties of an entity and entities (biological or otherwise). For biological entities the invention is the combination of a sonar sensor or sensors with an electric field sensor or sensors for the measurement of the structural and functional characteristics of organs and other structures where the electric field sensor does not have resistive contact with the surface of the organism, conferring multiple advantages. More particularly, the invention relates to sensors and sensor systems including devices and installations for assemblies for detecting sonar signatures in combination with electric potentials associated with a displacement signature within the geomagnetic field, and/or specific components and/or structures that are a component of that entity or entities. Specifically there is no resistive contact between the entity and the signal transduction component of the electric field sensor or sensors. Where the signals are amplified and combined to provide synergistic information about the properties of the entity. Other sensor types may be added in to provide further information such as for the identification of that entity.

Broadly defined, the present invention according to one aspect is a method of correlating sonic activity with electric activity in an entity of interest, including: interrogating, via a sonic sensor device, the physical structure, shape and/or form of an object in an entity of interest; interrogating, via an electric field sensor, the electric and/or magnetic potential associated with the object or the physical displacement of the geo-electric field by the object while avoiding resistive contact with other portions of the entity of interest; and linking results from the sonic sensor device to results from the electric field sensor.

In a feature of this aspect, the entity of interest is a living organism, and wherein the object in the entity of interest is a biological tissue.

In a further feature, the step of interrogating the electric and/or magnetic potential associated with the object or the physical displacement of the geo-electric field by the object while avoiding resistive contact with other portions of the entity of interest includes interrogating the electric and/or magnetic potential associated with the biological tissue or the physical displacement of the geo-electric field by the biological tissue while avoiding resistive contact with any external surface of the organism. In a still further feature, the method further includes a step of maintaining the electric field sensor at a distance of at least one micrometer from all external surfaces of the organism while carrying out the interrogating steps.

In another further feature, the object is a liver.

In another further feature, the object is a kidney.

In another further feature, the object is a heart.

In another further feature, the object is a brain.

In another further feature, the object is a muscle.

In another further feature, the object is a nerve.

In another further feature, the method further includes a preliminary step of implanting or temporarily placing the electric field sensor within the entity of interest at a location of at least one micrometer away from the object.

In another feature of this aspect, the method further includes a step of providing a plurality of electric field sensors around a central sonic sensor device.

In another feature of this aspect, the method further includes a step of arranging the sonic sensor device and the electric field sensor together within a single housing.

In another feature of this aspect, the sonic sensor device and the electric field sensor are not physically attached to each other.

In another feature of this aspect, the interrogating steps are carried out simultaneously.

In another feature of this aspect, the interrogating steps are carried out at different times.

Broadly defined, the present invention according to another aspect is a non-resistive contact electrosonic sensor system for correlating sonic activity with electric activity in an entity of interest, including: a sonic sensor device for interrogating the physical structure, shape and/or form of an object in an entity of interest; an electric field sensor for interrogating the electric and/or magnetic potential associated with the object or the physical displacement of the geo-electric field by the object while avoiding resistive contact with other portions of the entity of interest; control circuitry for linking results from the sonic sensor device to results from the electric field sensor.

In a feature of this aspect, the sonic sensor device is adapted to interrogate the physical structure, shape and/or form of a biological tissue in a living organism of interest, and the electric field sensor is adapted to interrogate the electric and/or magnetic potential associated with the biological tissue or the physical displacement of the geo-electric field by the biological tissue while avoiding resistive contact with other portions of the organism.

In a further feature, the electric field sensor is adapted to interrogate the electric and/or magnetic potential associated with the biological tissue or the physical displacement of the geo-electric field by the biological tissue while avoiding resistive contact with any external surface of the organism. In a still further feature, the electric field sensor is adapted to interrogate the electric and/or magnetic potential associated with the biological tissue or the physical displacement of the geo-electric field by the biological tissue while maintaining a distance of at least one micrometer from all external surfaces of the organism.

In another feature of this aspect, the electric field sensor includes a plurality of electric field sensors for interrogating the electric and/or magnetic potential associated with the object or the physical displacement of the geo-electric field by the object while avoiding resistive contact with other portions of the entity of interest, and wherein the plurality of electric field sensors is arranged around the sonic sensor device.

In another feature of this aspect, the sonic sensor device and the electric field sensor are disposed within a single housing.

In another feature of this aspect, the sonic sensor device includes an acoustic sensor.

In another feature of this aspect, the sonic sensor device includes an ultrasonic device.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein.

DETAILED DESCRIPTION

Figure 1:
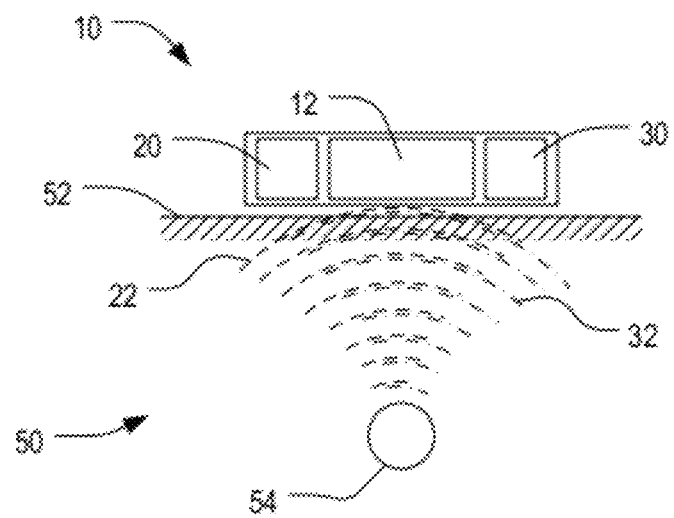
FIG. 1 is a block diagram of a non-resistive contact electrosonic sensor system in accordance with one or more preferred embodiments of the present invention

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, one or more preferred embodiments of the present invention are next described. The following description of one or more preferred embodiments is merely exemplary in nature and is in no way intended to limit the invention, its implementations, or uses.

FIG. 1 is a block diagram of a non-resistive contact electrosonic sensor system 10 in accordance with one or more preferred embodiments of the present invention. As shown therein, the non-resistive contact electrosonic sensor system 10 includes one or more sonic sensor devices 20 in combination with one or more dielectric or electric field sensors 30. Appropriate control circuitry and/or control logic 12 is also provided.

As used herein, the term "sonic" should be understood to mean or refer to the propagation of mechanical waves in gases, liquids, and solids, and includes vibration, sound, ultrasound, and infrasound. Furthermore, as used herein, the terms "sonic sensor" or "sonic sensor device" should be understood to mean or refer to a sensor or sensor device that is capable of detecting or sensing vibration, sound, ultrasound and/or infrasound mechanical waves.

Each sonic sensor device 20 includes a sonar transducer or the like that is adapted to detect a sound generated by a source 54 in an entity or entities 50 of interest. In many preferred embodiments, each entity 50 is a living organism and each source 54 is a biological tissue in that entity, such as a liver, a kidney, a mucous membrane or a brain, but it will be appreciated that in at least some embodiments, the entity 50 and/or source 54 could be something else, as described further below. Each sonic sensor may be disposed within a separate housing, or may be housed with other sensors or control circuitry/logic 12. The purpose of the sonic sensor or sensors is for interrogation of the physical structure, shape, and form of the source or sources 54 by either passive or active methods. Each sensor may be used to locate and determine the characteristics of a structure and its reference point's relationship to the placement of one or more electric field sensor. This can be used for more accurate placement and/or more accurate identification of the electric field signal source or sources. This information in turn provides useful data that may lead to more accurate metrics and may act as an aid to spatial reconstruction.

The electric field sensor (sometimes referred to herein as an "EFS") is provided for interrogation of the electric and/or magnetic potential associated with structures or the physical displacement of the geo-electric field by an entity. The electric field sensor does not have resistive contact with the entity that is being monitored. By not having resistive contact, the electric potentials associated with the internal structures (internal organs of a human, for example), as opposed to the electric potentials associated with the surface (such as the human's skin), can be measured. Furthermore, by not having resistive contact, the geomagnetic displacement signature of the entity can be measured.

In at least some embodiments, the electric field sensor signal transduction is preferably separated by at least 1 micrometer from the surface of the entity and/or from the source. In some embodiments, the electric potential sensor can be implanted or temporarily placed within the entity with the requirement of a membrane or structure separating the signal transduction component of the sensor from the tissue of interest or other source.

The signal transduction for the sonic sensor device or devices can occur at the surface 52 of the entity 50 or source 54, at an internal layer of the entity 50 or source 54, at a distance from the entity 50 or source 54, or any combination thereof. The amplified electric field sensor has high impedance input, where signal transduction is separated by at least 1 micrometer from the surface 52 of the entity 50 and/or from the source 54.

Although in the non-resistive contact electrosonic sensor system 10 of FIG. 1 the sonic sensor 20 is integrated with the electric field sensor 30, it will be appreciated that in accordance with at least some aspects of the present invention, the sensors 20,30 are not necessarily tethered to one another spatially or temporally. For example, an ultrasound probe may be used as a sonic sensor 20 to identify a structure for the best placement of electric field sensors 30. The placement area is marked and the ultrasound probe 20 is withdrawn. The electric field sensors 30 are then placed on the placement area and data is collected. In this use case the sonic sensor 20 and electric field sensor 30 are not tethered in time or space.

Sonar and other sonic sensors 20, both passive and active, inform on physical shape and distance, while electric field sensors 30 inform on electric or magnetic characteristics and distance. By combining the sensors, synergistic and cross-validating information is obtained, thereby adding a new level of functionality. More effective structural and functional imaging reconstruction may be achieved.

Figure 2:
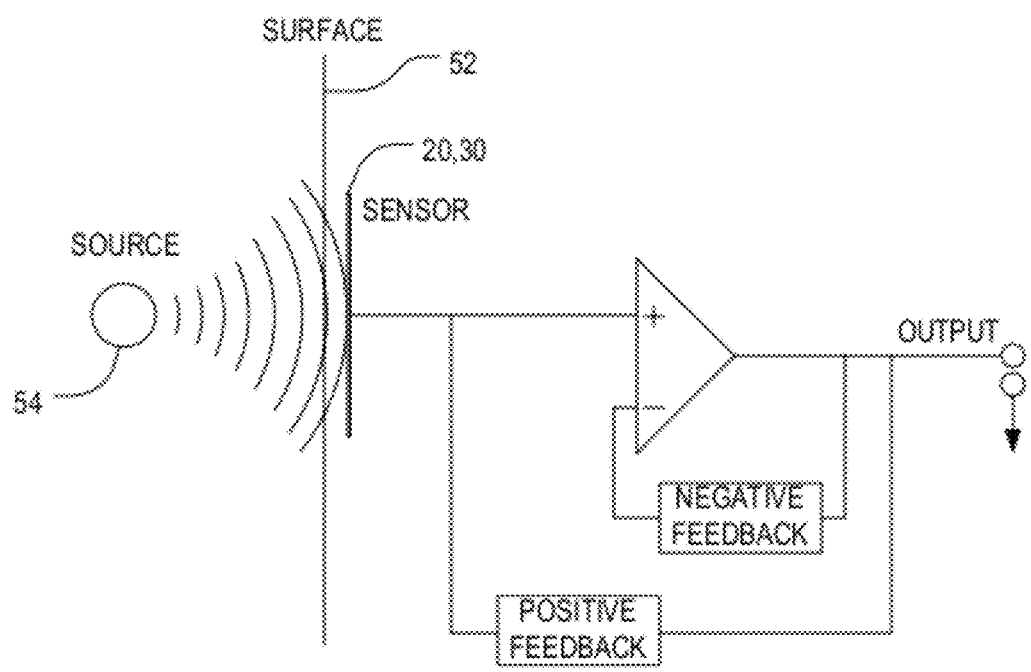
FIG. 2 is a schematic diagram illustrating the general operation of either of the sensors (acoustic or electric field) of FIG. 1.

FIG. 2 is a schematic diagram illustrating the general operation of either of the sensors 20,30 (sonic or electric field) of FIG. 1. For either sensor type, the entity of interest 50 serves as the source of the signals of interest 22,32. In at least some embodiments, there is a requirement for the dielectric (electric field sensor 30) to have no resistive contact. The signal 22,32 is amplified. The respective signal 22,32 may be subject to positive feedback for further amplification and refinement of the signal or negative feedback to optimize the gain of the signal.

In accordance with one aspect of the invention a sonic sensor 20 is used to identify and characterize a target structure and any other structures that may interfere with the electric or magnetic field. The electric field sensor 30 is used to characterize the electric or magnetic field properties of the target and other structures. As noted previously, the sensors 20,30 may be physically coupled or separate.

Figures 3A, 3B:
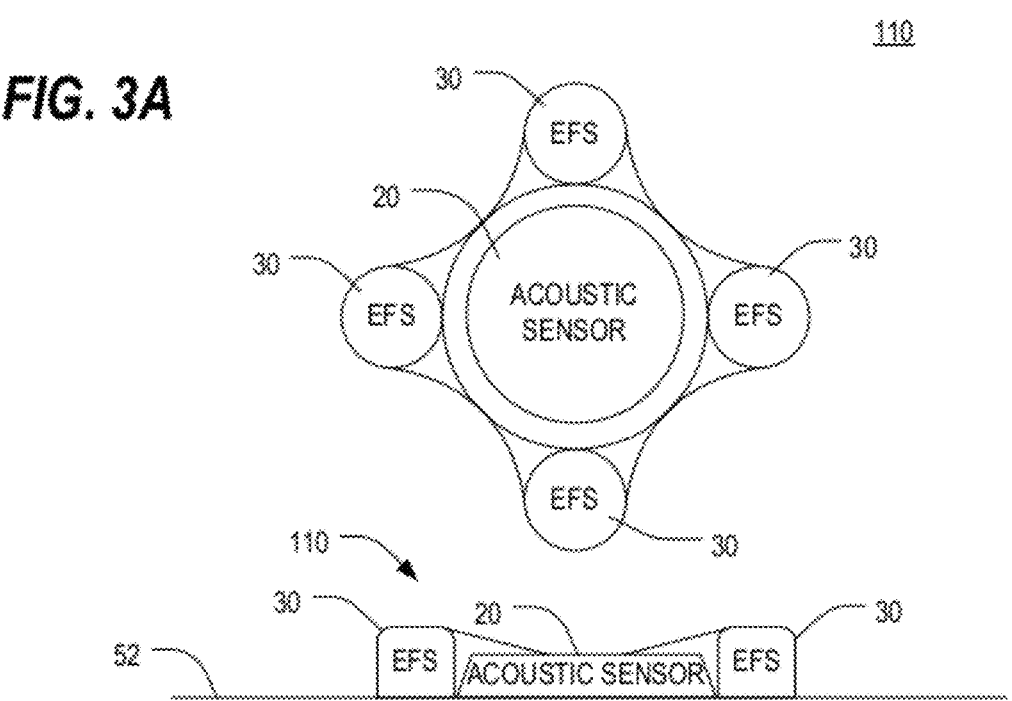
FIGS. 3A and 3B are a top and side view of a non-resistive contact electrosonic sensor system arranged in the form of a stethoscope.
Figure 4:
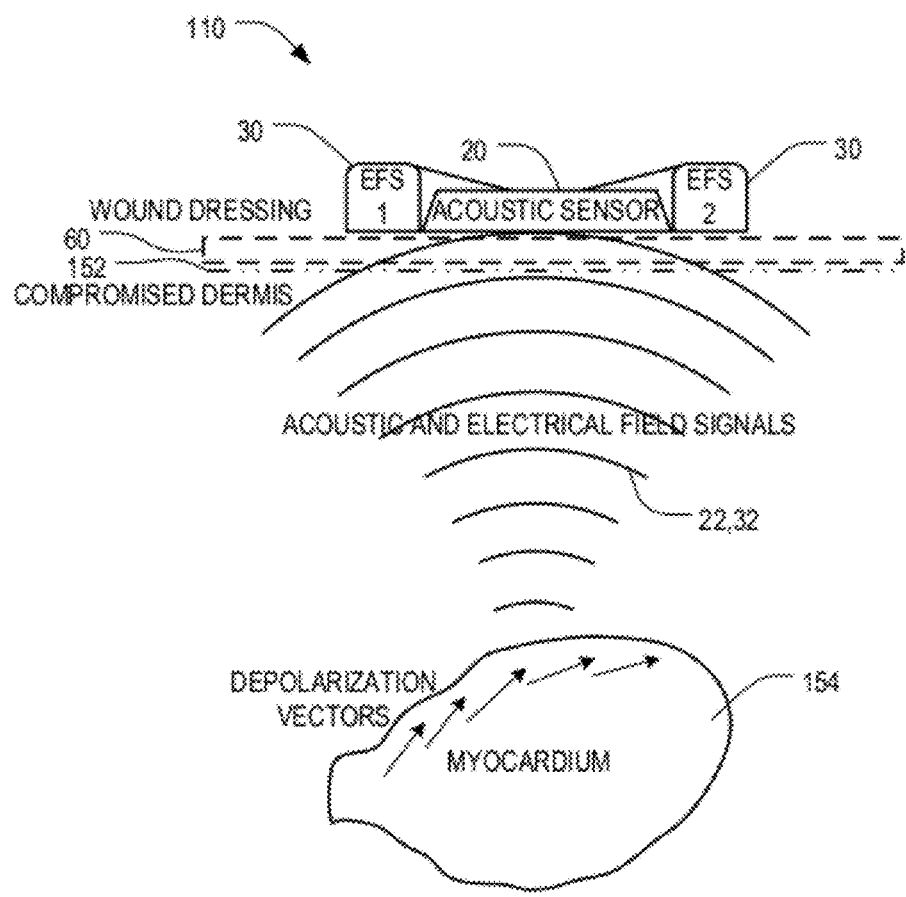
FIG. 4 is a schematic diagram illustrating the use of the stethoscope-type system of FIGS. 3A and 3B for correlating heart sounds with electrical activity of myocardium.

The combination of one or more sonic sensors with one or more electric field sensors in the manner described herein has applicability in a variety of embodiments and contexts. For example, FIGS. 3A and 3B are a top and side view of a non-resistive contact electrosonic sensor system 110 arranged in the form of a stethoscope. As shown therein, such a system 110 may include a central sonic sensor 20 surrounded by four EFSs 30. The stethoscope-type system 110 of FIGS. 3A and 3B has a high level of clinical functionality and may be used, for example, to correlate heart sounds with electrical activity of myocardium, thereby facilitating the assessment of a heart 54 through clothing, wound dressings, fur, and the like 60. The electrical activity of the myocardium as illustrated as depolarization vectors where a wave of depolarization flows from one area of the heart to the next during normal cardiac electrical systole, thus producing "depolarization vectors." FIG. 4 is a schematic diagram illustrating the use of the stethoscope-type system 110 of FIGS. 3A and 3B for such a purpose. This electric field stethoscope 110 can measure electric potentials through clothing, wound dressings, fur and/or any other impediment 60 to resistive contact and usefully combined with acoustic or ultrasound signals to provide valuable information about the status of an individual, animal or a non-biological entity. Notably, because such a device 110 does not require skin contact, it is particularly suitable for use over an area of skin 52 that has been compromised due to injury or the like and may be covered may be a wound dressing 60.

Figure 5:
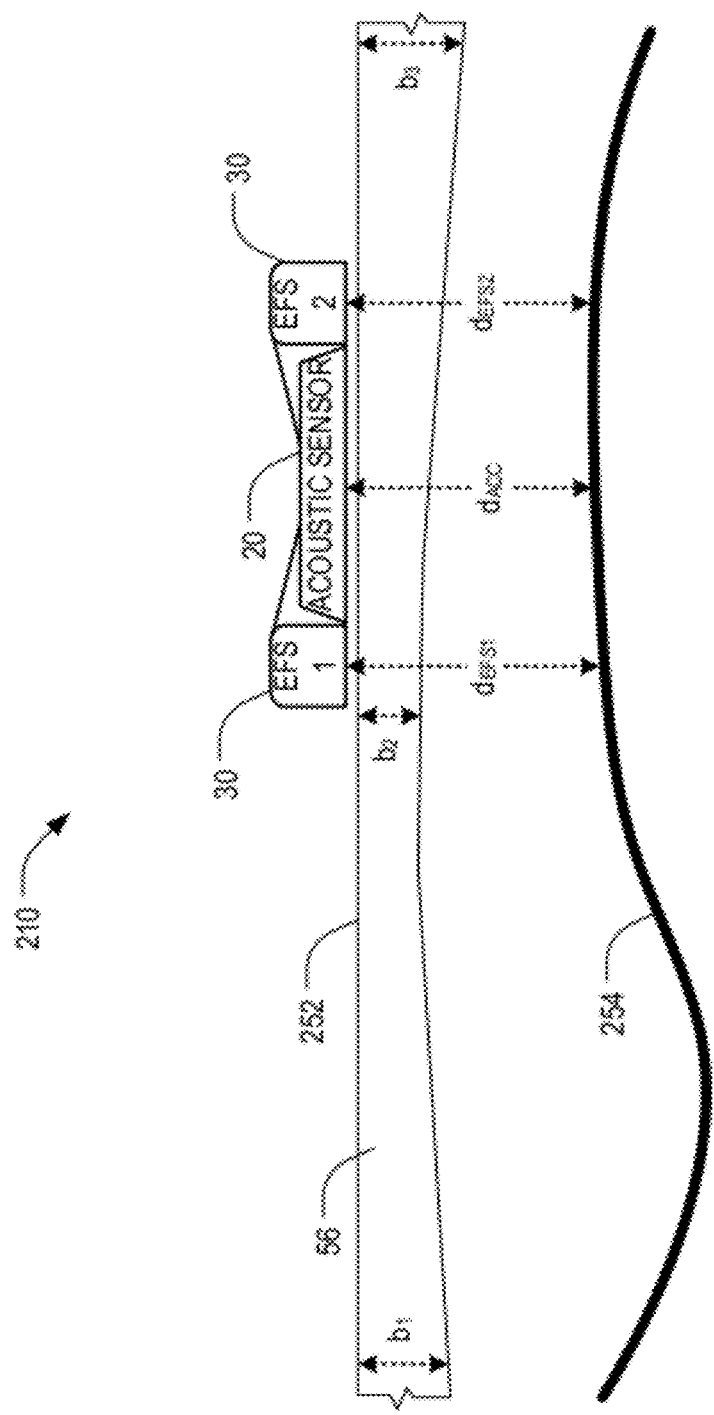
FIG. 5 is a schematic diagram of a non-resistive contact electrosonic sensor system for use in the structural and functional visualization of a nerve in accordance with another embodiment of the present invention.

The combined sensors 20,30 can be used for visualization and location of a nerve 54 for accurate acquisition of electric potential signature. FIG. 5 is a schematic diagram of a non-resistive contact electrosonic sensor system 210 for use in the structural and functional visualization of a nerve 254 in accordance with another embodiment of the present invention. The ultrasound or other sonic device images the nerve 254, using known and established principles of clinical ultrasound, determining the best anatomic location for placement of at least a pair of electric field sensors EFS1, EFS2 without resistive contact. The sonic sensor 20 determines the distance from the target 254 and also determines characteristics of tissue 56 overlying the target 254. The breadth or thickness $b_i$ of adipose tissue 56, which has higher electrical impedance, is determined at various locations by ultrasound. Three particular thicknesses in the arrangement of FIG. 5 are represented by $b_1$, $b_2$, and $b_3$, but it will be apparent that any number of thicknesses may be determined; i.e., that the thickness of the tissue 56 may be characterized in as much detail as desired. For optimal placement, the EFSs 30 are placed in an area where the nerve 254 is closest to the surface 252, and ideally each electric field sensor 30 is close to the same distance from each other (i.e., where $d_{EFS1}$ is approximately equal to $d_{EFS2}$). Furthermore sensor placement ideally occurs at a place where the adipose tissue 56 is relatively minimal and is close to the same thickness at different sensor locations (i.e., where $b_{EFS1}$ is approximately equal to $b_{EFS2}$). This information helps aids in interpretation of the electric field signal and also the placement of the electric field sensors 30.

The electric field signal output is a voltammetric signature recorded as the difference between the recording and the reference electrode/s where the reference electrodes would generally be orthogonal to both recording electrodes. (In at least some embodiments, the electric field sensors 30 would be recording electrodes, and the reference electrodes would be orthogonal to them.) Using this approach, the nerve conduction velocity may be obtained. The target voltammetric signature can be determined by subtracting known noise and by restricting bandwidth to known frequencies of the signal of interest. A further use of the sonic sensor 20 during this phase is for the detection of muscle movement, thereby aiding in the subtraction or cancelation of the muscle noise component of the signal.

To optimize the outcome, studies comparing normal individuals to those with known nerve conduction problems may be done so that patterns of nerve damage using this new technique could be recognized. This approach has advantages for the diagnosis of nerve damage or compromise by comparing to normal neural signal activity in control populations. Currently nerve damage is diagnosed with invasive fine needle nerve conduction studies. This technology can allow non-perturbative diagnosis saving considerable time and money and preventing negative side effects associated with invasive studies.

Another advantage would be for compartment pressure testing where nerves may be compromised through high internal compartment pressures. Diagnosis of this would be by comparing normal population with individuals with the known condition. Pattern analysis and comparison of the data results in pattern identification leading to pattern recognition software developed especially for this purpose. Currently diagnosis of high compartment pressures involves invasive procedures where a catheter is inserted into the compartment and the pressure is read through a pressure transducer. This technology may replace that technology as a diagnostic device. The technology, especially when implanted, could also be used to record neural output to control a prosthetic or other device as when a nerve has been severed or there is the desire to control a distant machine for any reason. The technology could also be used for recording the neural output from the autonomic nervous system for diagnosis, monitoring and treatment of a variety of conditions including emotional stress, depression, post traumatic stress disorder, epilepsy. For biofeedback this technology could be used to optimize performance through feedback control of autonomic outputs.

Figure 6:
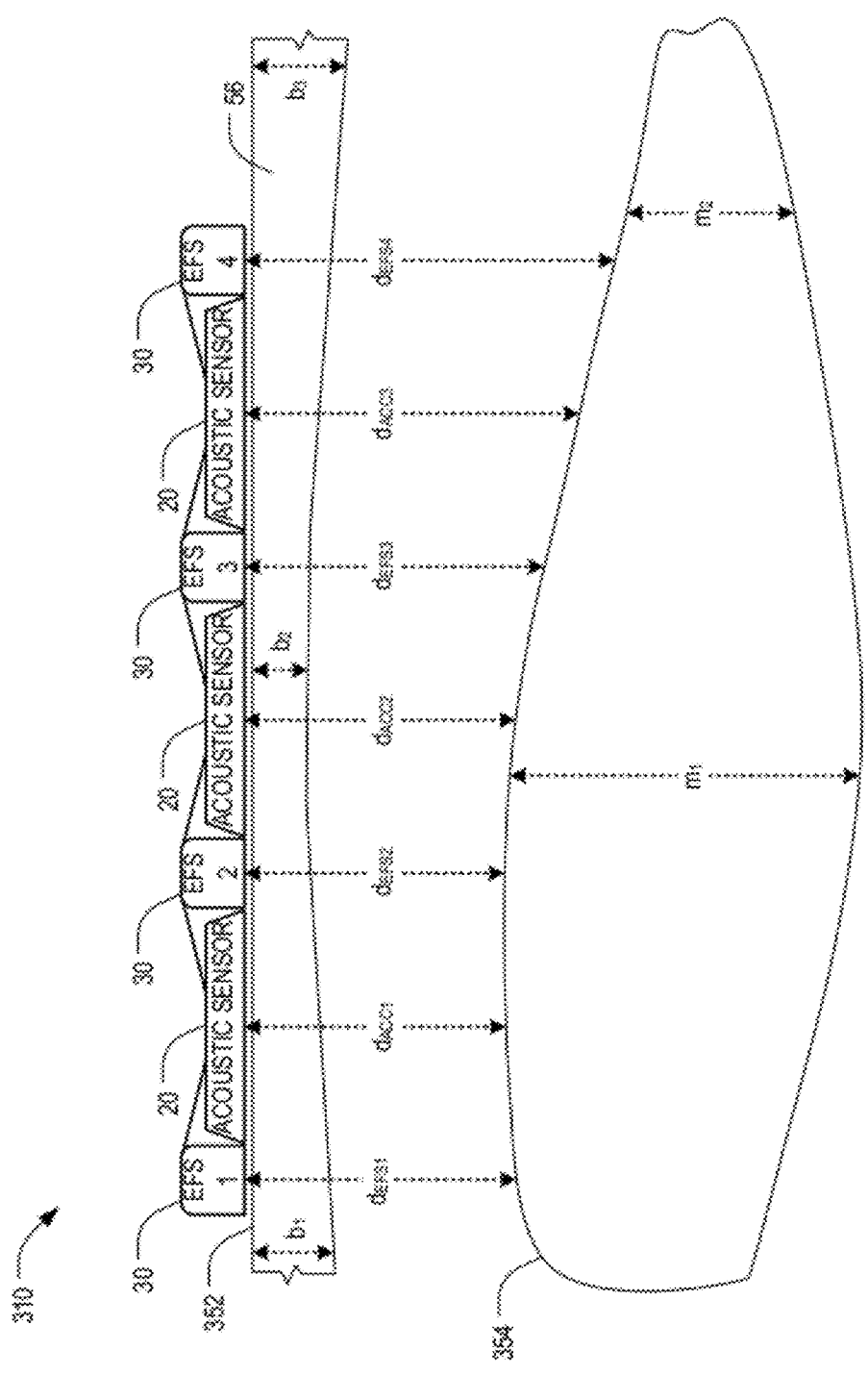
FIG. 6 is a schematic diagram of a non-resistive contact electrosonic sensor system for use in the structural and functional visualization of muscle in accordance with another embodiment of the present invention.

FIG. 6 is a schematic diagram of a non-resistive contact electrosonic sensor system 310 for use in the structural and functional visualization of muscle 354 in accordance with another embodiment of the present invention. Using this system, cardiac, skeletal or smooth muscle 354 may be visualized and the visualization may be correlated with movement and electrical and magnetic activity. This is useful for investigating correlations between structural and neural muscle damage. It is entirely non-invasive and provides information that may help diagnose and monitor a variety of conditions including infarction of the bowel, myocardial infarction, muscle trauma, muscular dystrophies and neurodegenerative conditions. As described above, this may also be able to be used for diagnosis of compartment syndrome. With high compartmental pressure muscles become starved of oxygen and that will change the electrical signature. Therefore the change in electric signature may be used to diagnose the characteristic decrease in perfusion of muscles that occurs with compartment syndrome, replacing the need for invasive compartment pressure testing.

Figure 7:
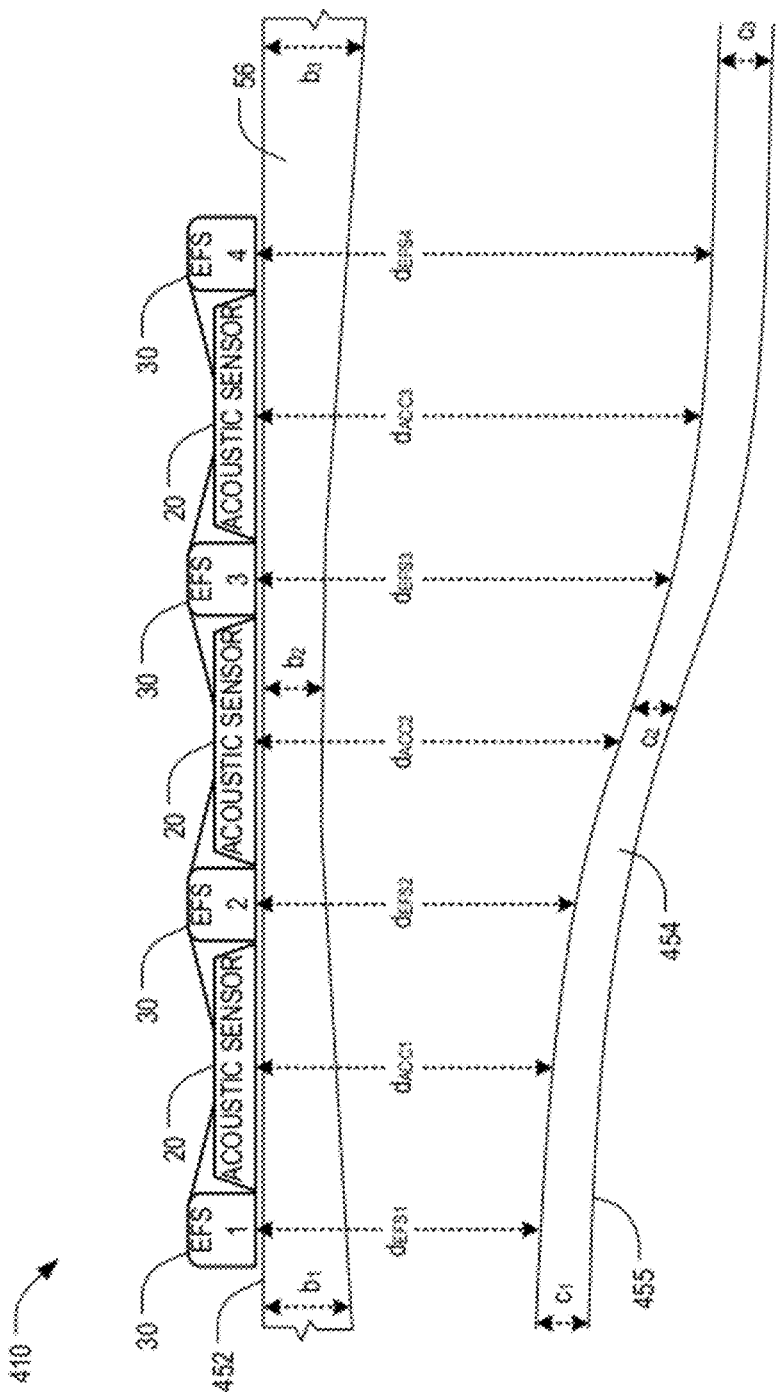
FIG. 7 is a schematic diagram of a non-resistive contact electrosonic sensor system for use in imaging fluid flowing through a conduit in accordance with another embodiment of the present invention.

FIG. 7 is a schematic diagram of a non-resistive contact electrosonic sensor system 410 for use in imaging fluid 454 flowing through a conduit 455 in accordance with another embodiment of the present invention. It will be appreciated that a fluid, especially one flowing through a material that differs in impedance from that of the fluid, generates an electromagnetic signature. Sonic sensing can be used to pick up characteristics of fluids 454 and conduit walls 455 through active sonar or other sonic sensing while electric field sensing can be used to pick up this electromagnetic signature. This has use for diagnosing and monitoring blood flow and may be useful for triaging of casualties, or monitoring vessel blockage and/or compromise. This may replace current technologies, many of which are invasive.

It will be appreciated that although the system 410 illustrated in FIG. 7 may be particularly suitable for biological purposes, but it could also be used for non-biological purposes such as for identification of underground fluid reserves or for rivers.

Figure 8:
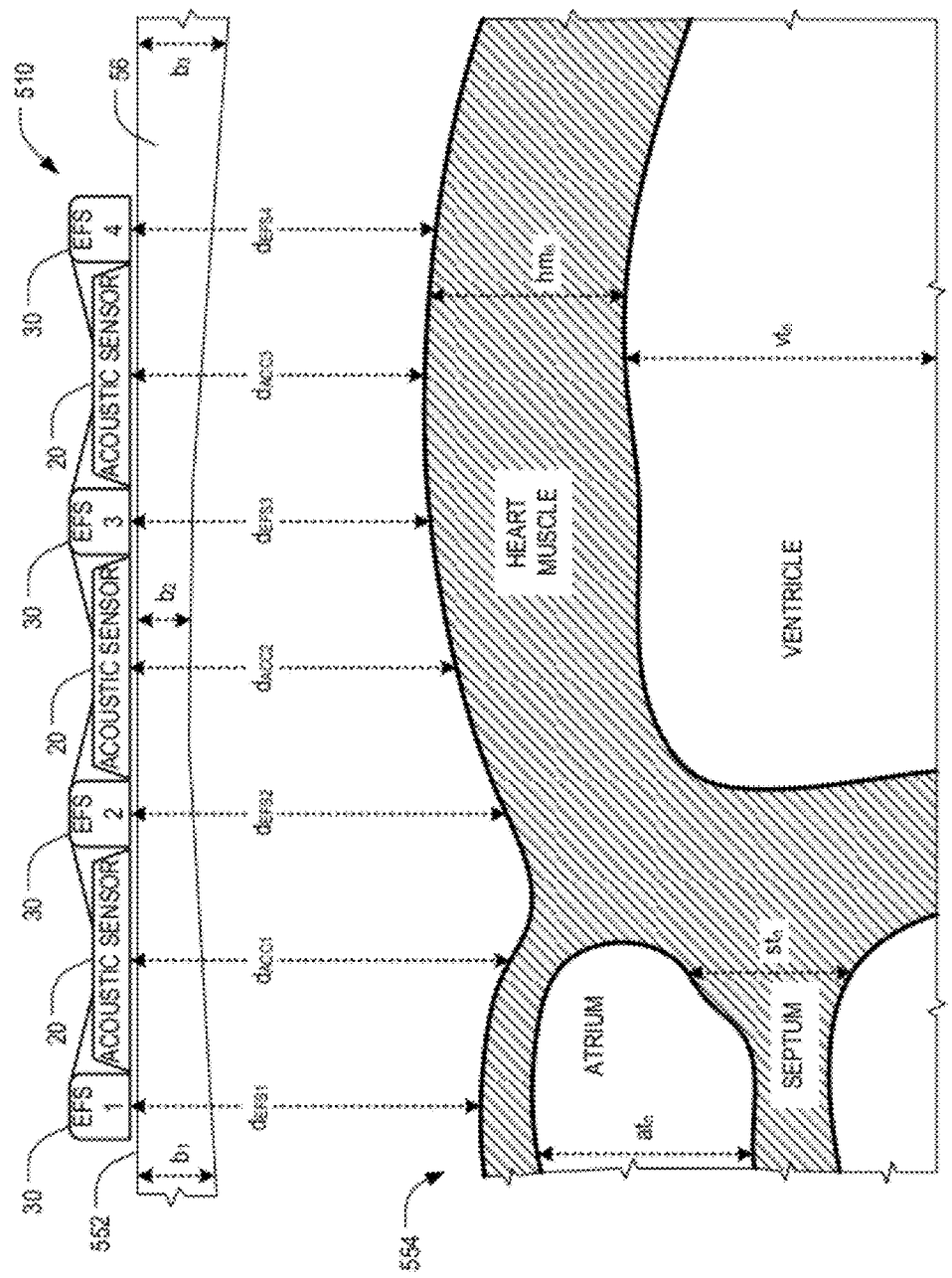
FIG. 8 is a schematic diagram of a non-resistive contact electrosonic sensor system for use in combining structural, electrical and fluid dynamic information for more complete imaging in accordance with another preferred embodiment of the present invention.

FIG. 8 is a schematic diagram of a non-resistive contact electrosonic sensor system 510 for use in combining structural, electrical and fluid dynamic information for more complete imaging in accordance with another preferred embodiment of the present invention. The signature acquisition of the various structures is described above. Put together the invention may inform on the electrical activity of the cardiac muscle, the structural integrity and movement of the cardiac muscle, and the outflow from the chambers of the heart 554 itself. The combined technology will provide a high level of clinical information and may inform on diagnosis, effect of treatment and progression of disease of the heart 554. The same application can be made to a variety of other organs within the body including the: lungs, liver, kidneys, bladder, skin, spleen, pancreas and bowel. The sensor in an array may also inform on the structure and function of the central spinal cord and of the brain.

Figure 9:
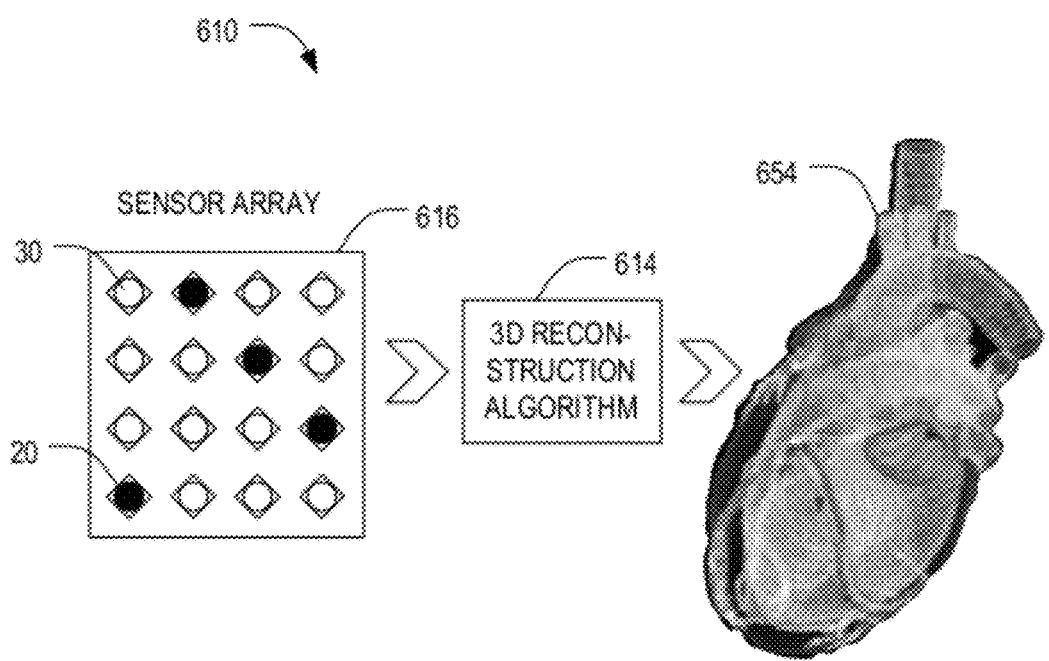
FIG. 9 is a schematic diagram of a non-resistive contact electrosonic sensor system using an array of acoustic sensors and EFSs to produce a three-dimensional image of an internal organ, all in accordance with another preferred embodiment of the present invention.

FIG. 9 is a schematic diagram of a non-resistive contact electrosonic sensor system 610 using an array 616 of sonic sensors and EFSs to produce a three-dimensional image of an internal organ, all in accordance with another preferred embodiment of the present invention. As shown therein, four sonic sensors 20 (black circles) and twelve EFSs 30 (white circles) are used to gather data regarding a heart 654. A 3D reconstruction algorithm 614 is then utilized to produce a three-dimensional image of the heart.

Figure 10:
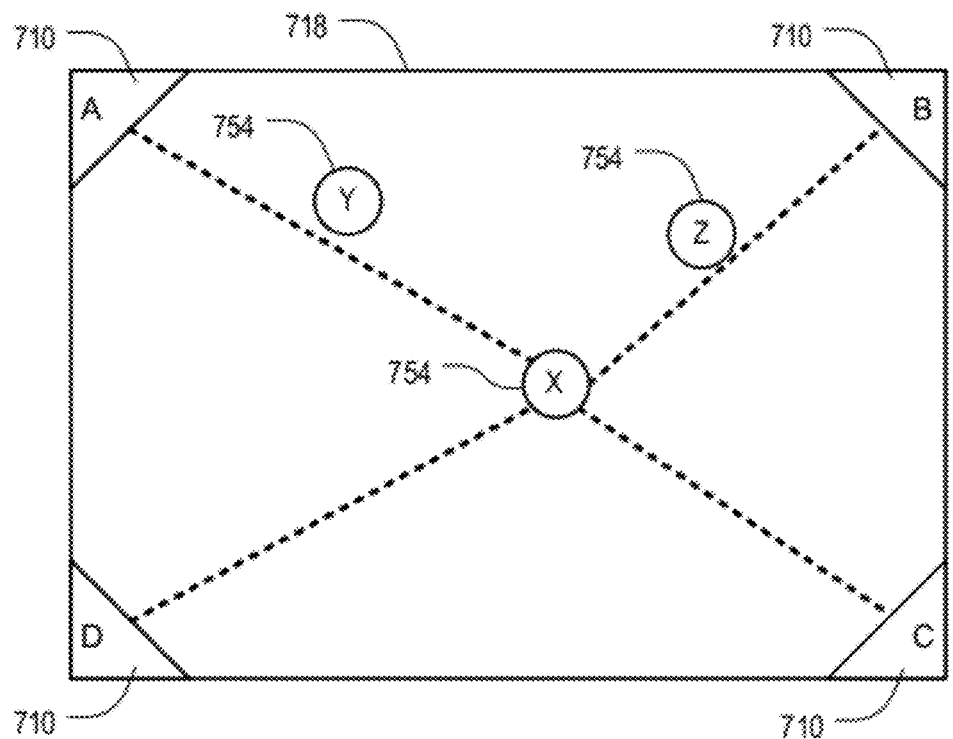
FIG. 10 is a schematic diagram of a multi-unit non-resistive contact electrosonic sensor system for use in monitoring people or other entities in a room in accordance with another embodiment of the present invention.

In accordance with another aspect of the invention, a sensor assembly for use with an entity may include a series of non-resistive contact electrosonic sensor devices linked together in a unified system, wherein each electrosonic sensor device is a combination of at least one sonic sensor with electric field sensors for the monitoring of entity or entities. For example, FIG. 10 is a schematic diagram of a multi-unit non-resistive contact electrosonic sensor system 700 for use in monitoring people or other entities 754 in a room 718 in accordance with another embodiment of the present invention. As illustrated therein, a plurality of non-resistive contact electrosonic sensor devices 710 are arranged around the room 718. Each such device includes one or more sonic sensor 20, one or more electrical field sensor 30, or a combination of both. The sensors 20,30 may be used to distinguish person X from person Y and person Z by identifying and tracking their sonic or electric field signature, respectively. In the case of their sonic signature it may be actively determined from their shape or passively determined by characteristic features including voice, breathing and gait recognition. Their electric field signature may be identified through geomagnetic displacement information including reconstruction of shape and movement or characteristic electric field information such as the pattern and amplitude of their cardiac or respiratory characteristics. This technology could be used with a variety of other sensors or sensor systems to support other identifications, such as use with visual recognition systems. Unlike systems based only on visual recognition, however, the system of the present invention can sense remotely and thus could be used to track people 754 through walls or underground. It could also be used to identify machinery and to track it. This would be especially useful for equipment that has a strong electromagnetic presence including communications equipment.

In accordance with another aspect of the invention the electric field sensors could be combined with active technologies including tomographic techniques where an electric field is passed through an entity and the output at the other end is characterized by the electric field sensor or sensors.

In accordance with another aspect of the invention the sonic component could be used to detect sounds emitted from an organism such as breathing or talking and use these either alone or in combination with non-resistive contact electric field sensors or other sensor technologies for the diagnosis or monitoring of medical conditions including sleep apnea, heart failure, pneumonia, or hemothorax. The diagnosis of heart failure for example, may be aided by an altered resonant frequency in the bases of the lungs as vocal and/or breath sounds move through fluid, in combination with a change in the electric potential signature from the myocardium. This technology could be incorporated into a mobile phone device or the like.

In accordance with another aspect of the invention the sensors could be combined with a magnetometer or magnetometers to provide additional information about the entity. A combination electric field sensor and magnetometer would be useful as it would provide information about power usage of certain structures as power is a function of voltage, as measured by an electric field sensor and current, as measured by a magnetometer. In this case a sonic sensor or sensors could be used provide further information about the structure of the device or related objects and relate it to effects on power usage.

Figure 11:
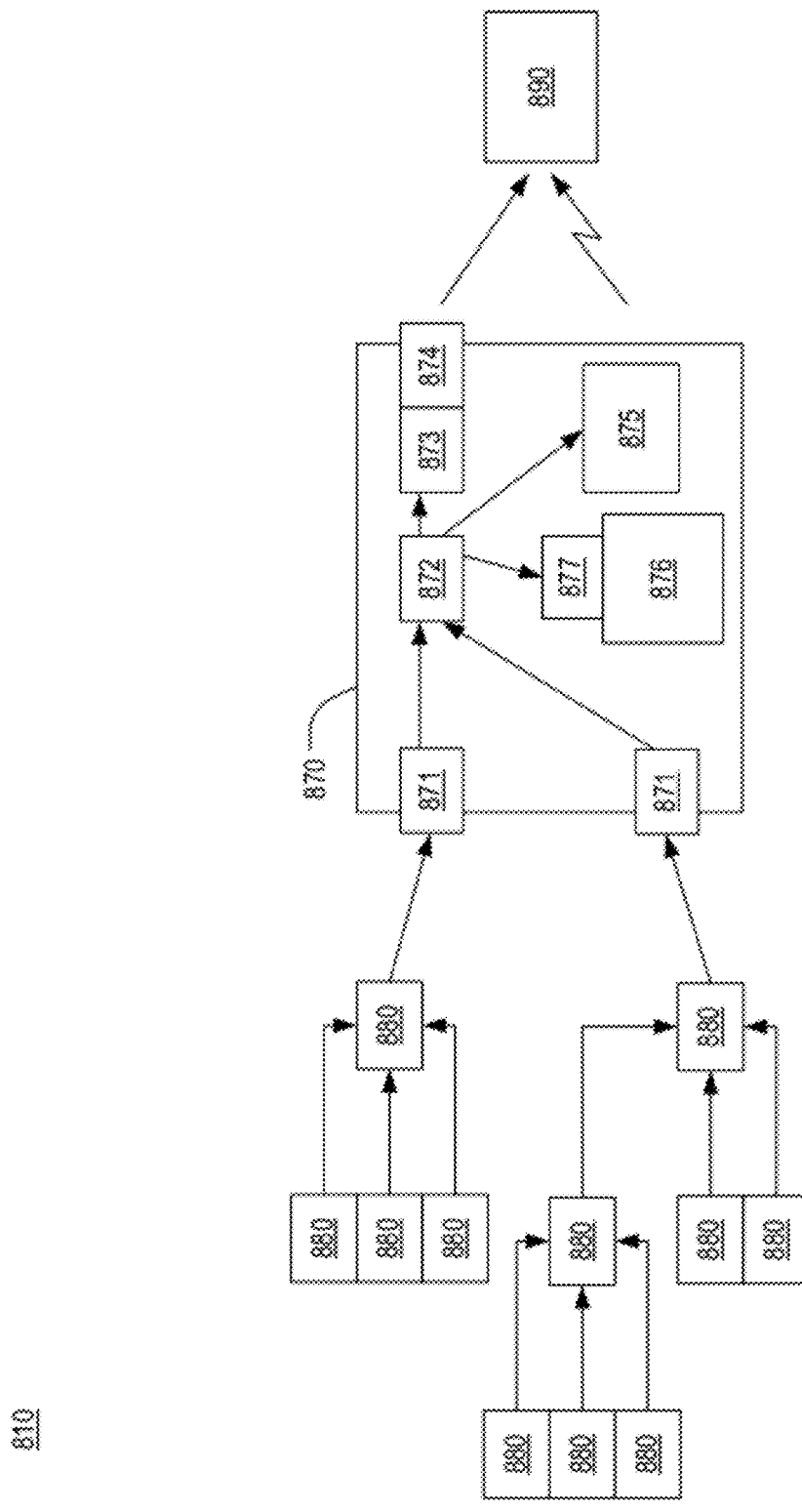
FIG. 11 is a block diagram illustrating the physical implementation of a non-resistive contact electrosonic sensor system in accordance with one or more preferred embodiments of the present invention.

FIG. 11 is a block diagram illustrating the physical implementation of a non-resistive contact electrosonic sensor system 810 in accordance with one or more preferred embodiments of the present invention. In particular, the system 810 is implemented in the form of a mother processing unit 870 and a plurality of sensor units 880. Each sensor unit 880 may have additional sensor units 880 connected thereto, thereby linking a potentially unlimited number of sensor units 880 back to the mother processing unit 870.

Figure 12:
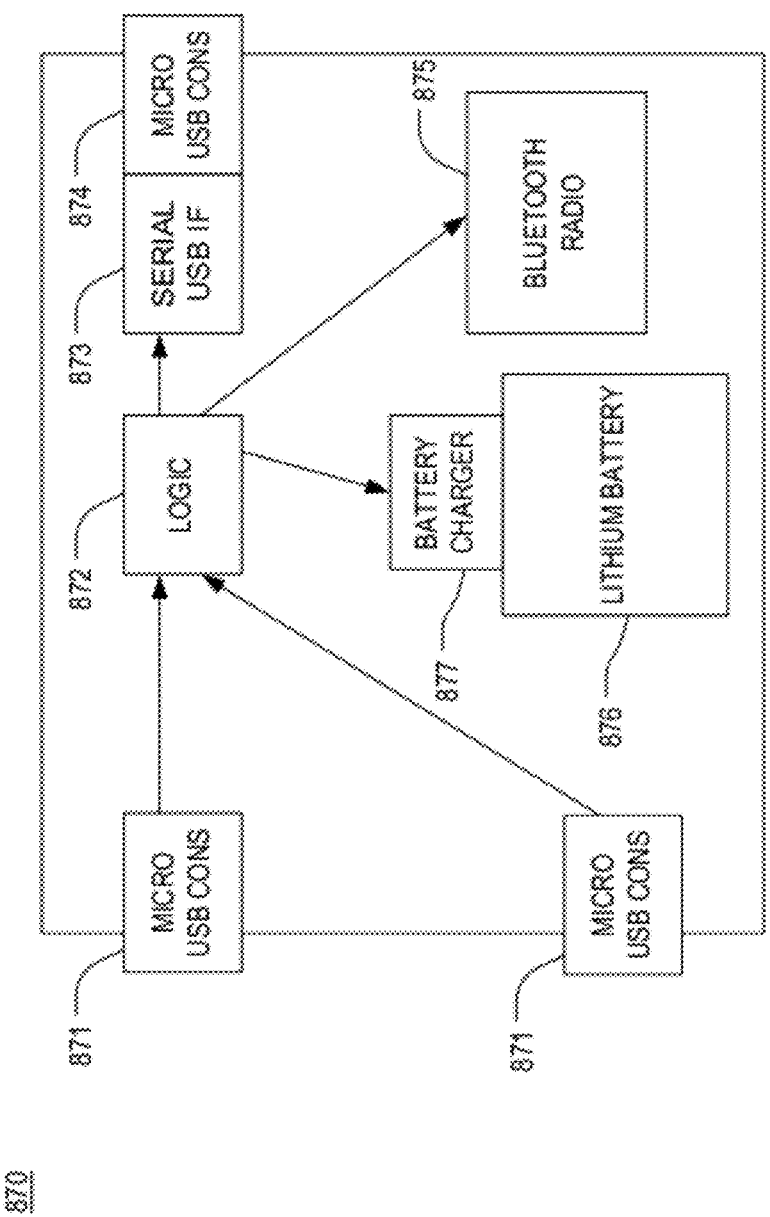
FIG. 12 is a block diagram of the mother processing unit of FIG. 11.

FIG. 12 is a block diagram of the mother processing unit 870 of FIG. 11. As shown in FIGS. 11 and 12, the mother processing unit 870 includes connectors 871, which are preferably micro USB connections, for physical connection to the sensor units 880. Communications from sensor units 880 are linked together by control logic (CPU) 872. Output communications (typically to a computer or other computing device 890) may be provided via serial USB interface 873/micro USB connection 874, bluetooth radio 875, or the like. An onboard lithium battery 876 and battery charger 877 are preferably provided for power.

Figure 13:
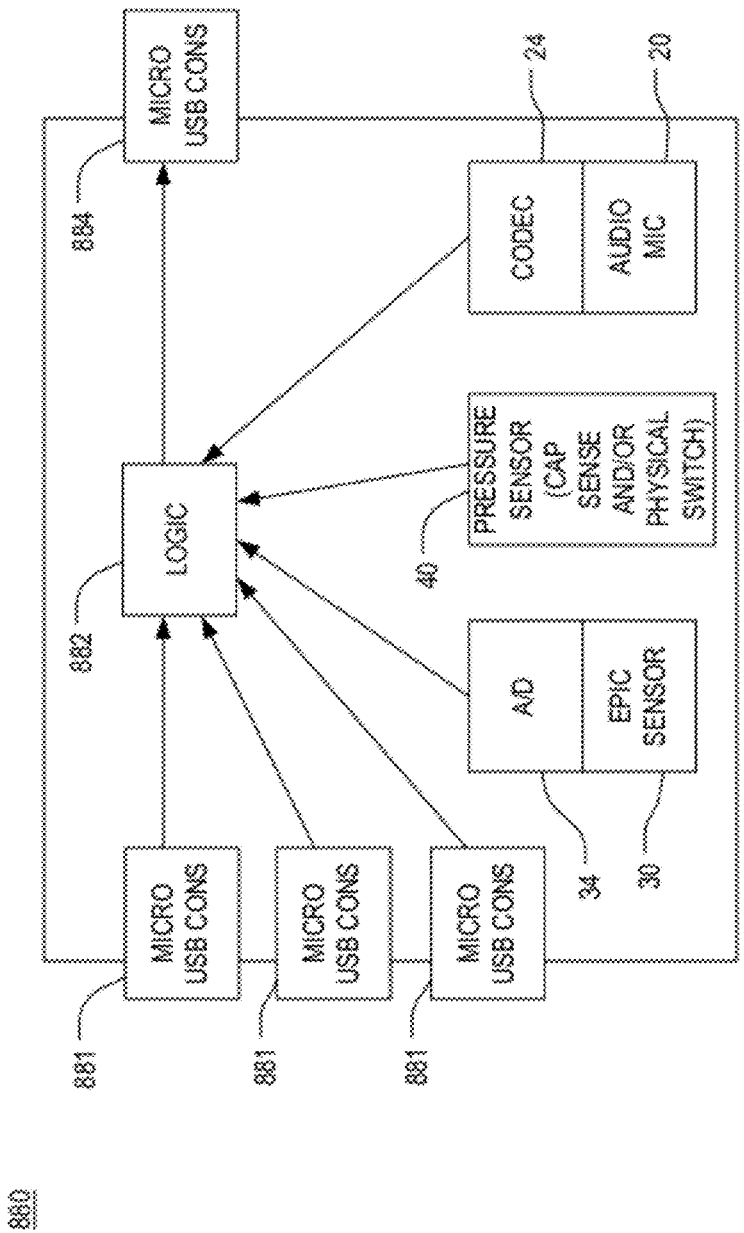
FIG. 13 is a block diagram of one of the sensor units of FIG. 11.

FIG. 13 is a block diagram of one of the sensor units 880 of FIG. 11. As shown therein, each sensor unit contains an electric field sensor 30 and an audio microphone 20, with an A/D converter 34 being provided for the EFS 30 and a codec 24 being provided for the microphone 20. The electric field sensor 30 is preferably a commercially-available EPIC (electric potential integrated circuit) sensor. In addition to the EFS (EPIC) sensor 30 and the microphone 20, a pressure sensor 40 is also preferably provided. The pressure sensor 40 may be, for example, a cap sense or physical switch-type sensor. Connectors 881,884, which are preferably micro USB connections and preferably match those on the mother processing unit, are provided for both physical connection to the mother processing unit 870 or to another sensor unit 880. Operation is controlled by central control logic (CPU) 882.

Figure 14:
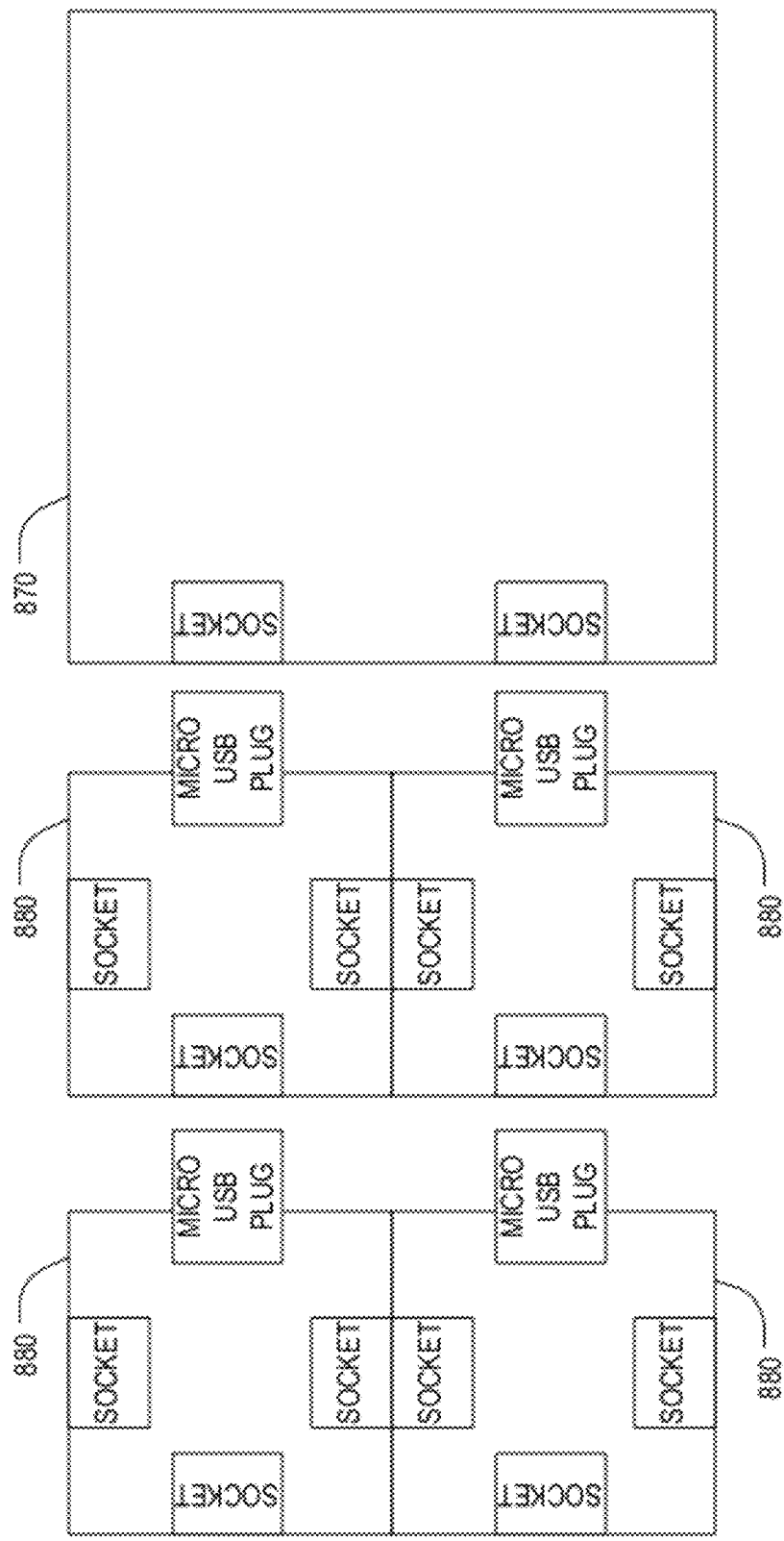
FIG. 14 is a block diagram illustrating an array expansion of the mother processing unit and sensor units of FIGS. 11-13 for possible use in a phone.
Figure 15:
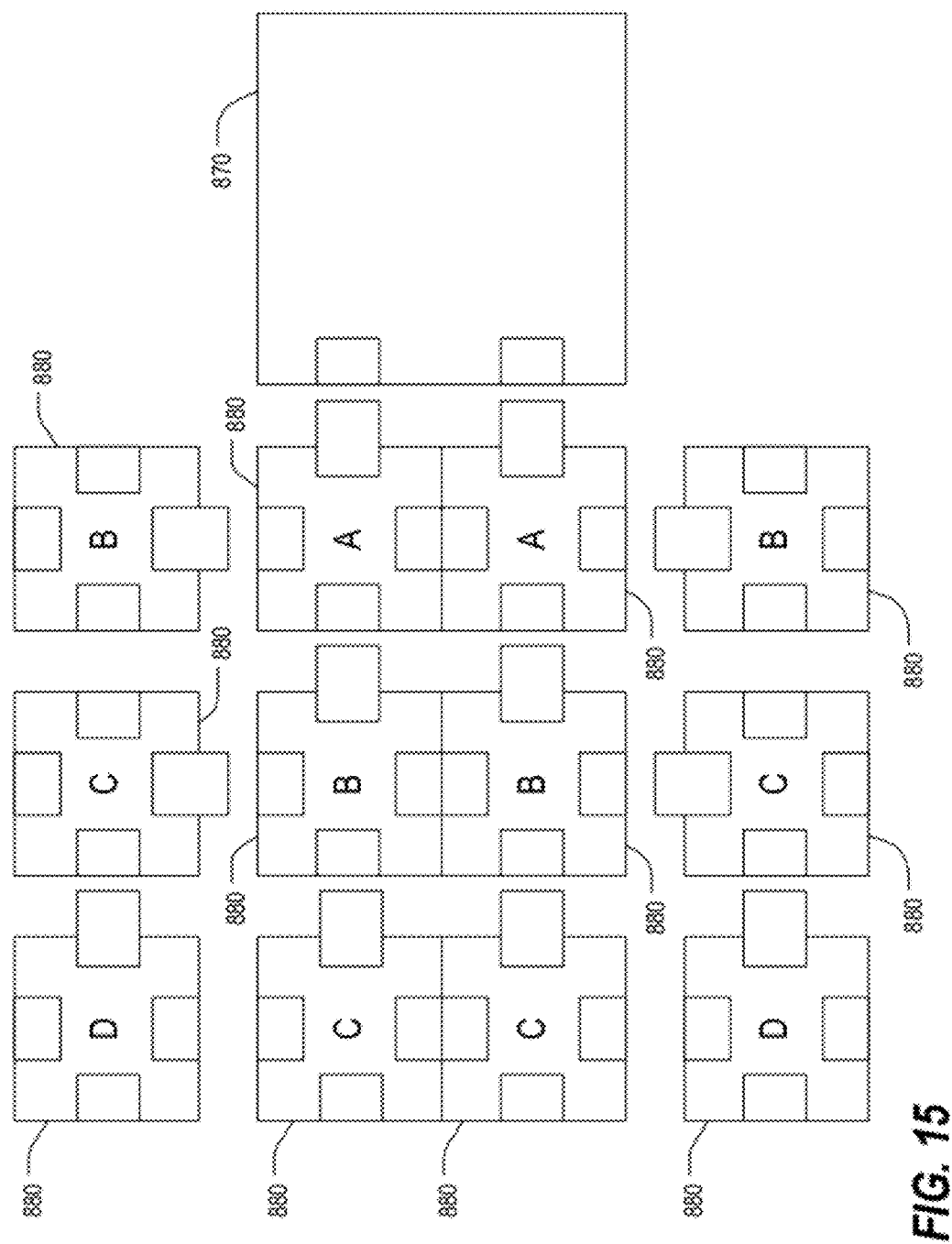
FIG. 15 is a block diagram illustrating a still-larger array expansion of the mother processing unit and sensor units of FIGS. 11-13.

The modular nature of each sensor unit 870 permits large arrays of nearly unlimited size to accommodate a wide variety of applications. FIG. 14 is a block diagram illustrating an array expansion of the mother processing unit 870 and sensor units 880 of FIGS. 11-13 for possible use in a phone, and FIG. 15 is a block diagram illustrating a still-larger array expansion of the mother processing unit 870 and sensor units 880 of FIGS. 11-13.

A variety of advantages are offered by one or more embodiments and/or aspects of the present invention. For example, there is no requirement for direct contact with the body, which itself has advantages when the skin integrity is compromised (as illustrated in FIG. 4), if a sensor is needed for sterile procedures, for remote monitoring, for electrical safety, in decreasing potential preparation time, in providing synergistic source information, in avoiding the need to collect data at the surface of the entity, and in avoiding invasive procedures.

Furthermore, a combined sonic and EFS (Electric Field Sensor) array will be able to: identify, locate and track entities, gain synergistic information about an entity, increase the information available for diagnoses, and increase the information available for carrying out biological structural and functional imaging.

For invasive procedures or implants the sensor can be enveloped in a biocompatible sleeve that: allows multiple reuse of the sensor, allows the sleeve to be disposed ensuring sterility of procedures, and allows a completely biocompatible shield to be placed around the sensor.

There is minimal interference with the signal being measured. That is, the technology is non-perturbative. This feature has the advantage that sensors do not interfere with the target signal allowing more effective structural and functional signal reconstruction.

When under stress, materials such as concrete and rock produce acoustic (sonic) and electromagnetic signatures. Therefore, application of the current invention may be used to detect the structural integrity of critical building structures. Likewise, the invention may be used to detect strain in rocks or other materials prior to a potentially catastrophic event such as an earthquake.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof.

What is claimed is:

1. A method for facilitating a medical diagnosis related to an internal object in an entity of interest utilizing one or more sonic sensors and a plurality of non-resistive contact electric field sensors, comprising:
   (a) determining physical characteristics of the entity of interest by detecting sound using the one or more sonic sensors when disposed at the entity of interest positioned proximate the internal object, the determined physical characteristics including a thickness of adipose tissue at a plurality of positions proximate the internal object;
   (b) positioning the plurality of non-resistive contact electric field sensors at the entity of interest by utilizing one or more of the determined physical characteristics of the entity of interest to select locations for positioning of the plurality of non-resistive contact electric field sensors, the locations being selected to have similar thicknesses of adipose tissue;
   (c) determining electric or magnetic potential of the internal object by detecting the internal object using the positioned plurality of non-resistive contact electric field sensors,
      (i) wherein each electric field sensor comprises a signal transduction component, and
      (iii) wherein during the detection using the electric field sensors no resistive contact occurs between the signal transduction components of the electric field sensors and any portion of the entity of interest; and
   (d) providing data from detecting the internal object using the positioned plurality of non-resistive contact electric field sensors to a medical practitioner;
   whereby data from the one or more sonic sensors and data from the plurality of non-resistive contact electric field sensors is utilized in combination to provide information for facilitating a medical diagnosis related to the internal object.

2. The method of claim 1, wherein the entity of interest is a living organism.

3. The method of claim 2, wherein said step (b) comprises maintaining the signal transduction component of each electric field sensor at a distance of at least one micrometer from contact with the organism.

4. The method of claim 2, wherein the object comprises a liver, a kidney, a heart, a brain, a muscle, a lung, a bladder, a spleen, a pancreas, a bowel, or a nerve.

5. A method for facilitating a medical diagnosis related to an internal object in an entity of interest utilizing one or more sonic sensors and a plurality of non-resistive contact electric field sensors, comprising:
   (a) determining physical characteristics of the entity of interest by detecting sound using the one or more sonic sensors when disposed at the entity of interest positioned proximate the internal object, the determined physical characteristics including a thickness of adipose tissue at a plurality of positions proximate the internal object;
   (b) positioning the plurality of non-resistive contact electric field sensors at the entity of interest by utilizing one or more of the determined physical characteristics of the entity of interest to select locations for positioning of the plurality of non-resistive contact electric field sensors, the locations being selected to have similar thicknesses of adipose tissue;
   (c) determining electric or magnetic potential of the internal object by detecting the internal object using the positioned plurality of non-resistive contact electric field sensors,
      (i) wherein each electric field sensor comprises a signal transduction component, and
      (iii) wherein during the detection using the electric field sensors no resistive contact occurs between the signal transduction components of the electric field sensors and any portion of the entity of interest; and
   (d) providing data from detecting the internal object using the positioned plurality of non-resistive contact electric field sensors to a medical practitioner;
   (e) wherein the sonic sensor and the electric field sensors are integrated within a single housing; whereby data from the one or more sonic sensors and data from the plurality of non-resistive contact electric field sensors is utilized in combination to provide information for facilitating a medical diagnosis related to the internal object.

6. The method of claim 5, wherein the entity of interest is a living organism.

7. The method of claim 5, wherein said step (b) comprises maintaining the signal transduction component of each electric field sensor at a distance of at least one micrometer from contact with the organism.

8. The method of claim 5, wherein the object comprises a liver or a kidney.

9. The method of claim 5, wherein the object comprises a heart.

10. The method of claim 5, wherein the object comprises a brain.

11. The method of claim 5, wherein the object comprises a muscle.

12. The method of claim 5, wherein the object comprises a bladder.

13. The method of claim 5, wherein the object comprises a spleen.

14. The method of claim 5, wherein the object comprises a pancreas.

15. The method of claim 5, wherein the object comprises a bowel.

16. The method of claim 5, wherein the object comprises a nerve.

17. A method for facilitating a medical diagnosis related to an internal object in an entity of interest utilizing one or more sonic sensors and a plurality of non-resistive contact electric field sensors, comprising:
   (a) determining physical characteristics of the entity of interest by detecting sound using the one or more sonic sensors when disposed at the entity of interest positioned proximate the internal object, the determined physical characteristics including a thickness of adipose tissue at a plurality of positions proximate the internal object;
   (b) positioning the plurality of non-resistive contact electric field sensors at the entity of interest by utilizing one or more of the determined physical characteristics of the entity of interest to select locations for positioning of the plurality of non-resistive contact electric field sensors, the locations being selected to have similar thicknesses of adipose tissue;

(c) determining electric or magnetic potential of the internal object by detecting the internal object using the positioned plurality of non-resistive contact electric field sensors,
  (i) wherein each electric field sensor comprises a signal transduction component, and
  (iii) wherein during the detection using the electric field sensors no resistive contact occurs between the signal transduction components of the electric field sensors and any portion of the entity of interest; and
(d) providing data from detecting the internal object using the positioned plurality of non-resistive contact electric field sensors to a medical practitioner;
(e) wherein the sonic sensor and the electric field sensors are part of a stethoscope;
whereby data from the one or more sonic sensors and data from the plurality of non-resistive contact electric field sensors is utilized in combination to provide information for facilitating a medical diagnosis related to the internal object.

18. The method of claim 17, wherein the entity of interest is a living organism.

19. The method of claim 18, wherein said step (b) comprises maintaining the signal transduction component of each electric field sensor at a distance of at least one micrometer from contact with the organism.

20. The method of claim 17, wherein the object comprises a liver, a kidney, a heart, a brain, a muscle, a lung, a bladder, a spleen, a pancreas, a bowel, or a nerve.

\* \* \* \* \*